United States Patent [19]

Tiemann et al.

[11] Patent Number: 5,349,954
[45] Date of Patent: Sep. 27, 1994

[54] TUMOR TISSUE CHARACTERIZATION APPARATUS AND METHOD

[75] Inventors: Jerome J. Tiemann, Schenectady; Fay A. Marks, Waterford, both of N.Y.

[73] Assignee: General Electric Company, Schenectady, N.Y.

[21] Appl. No.: 95,462

[22] Filed: Jul. 23, 1993

[51] Int. Cl.$^5$ ............................................. A61B 6/00
[52] U.S. Cl. .................................. 128/634; 128/665; 128/751; 128/749
[58] Field of Search ............... 128/634, 633, 664–666, 128/749, 751–755, 763, 765, 768, 771; 604/272

[56] References Cited

U.S. PATENT DOCUMENTS

| | | | |
|---|---|---|---|
| 4,586,513 | 5/1986 | Hamaguri | 128/633 |
| 5,048,524 | 9/1991 | Bailey | 128/634 |
| 5,078,142 | 1/1992 | Siczek et al. | 128/653.1 |
| 5,078,150 | 1/1992 | Hara et al. | 128/634 |
| 5,092,331 | 3/1992 | Nakamura et al. | 128/634 |
| 5,127,408 | 7/1992 | Parsons et al. | 128/634 |
| 5,167,686 | 12/1992 | Wong | 128/634 |
| 5,199,431 | 4/1993 | Kittrell et al. | 128/634 |

OTHER PUBLICATIONS

"The Optical Biopsy System" by Irving J. Bigio, et al., Los Alamos National Laboratory, Los Alamos, N. Mex. 87545, Mar. 1992, pp. 1–9.
"Fiber Optic Relectance Spectrophotometry System for In Vivo Tissue Diagnosis" by Kimizo Ono, et al., Applied Optics, vol. 30, No. 1, Jan. 1991, pp. 98–105.
"Micro–light Guides: A New Method for Measuring Tissue Fluorescence and Reflectance" by Sungchul Ji, et al., The American Physiological Society, vol. 236, Mar. 1979, pp. C147–C156.
"Physiolotical Monitoring and Early Detection Diagnostic Methods" by the Society of Photo–Optical Instrumentation Engineers, Proceedings Reprint, SPIE—The International Society for Optical Engineering, Jan. 22–23, 1992, Los Angeles, Calif., vol. 1641.
"Optical Spectroscopy (INVOS) is Unreliable in Detecting Breast Cancer" by Carol Mae Bosanko, et al., AJR 155:43–47.
"The Erlangen Micro–Lightguide Spectrophotometer", K. H. Frank, et al., Phys. Med. Biol., 1989, vol. 34, No. 12, 1883–1900.

Primary Examiner—Lee S. Cohen
Assistant Examiner—Robert L. Nasser, Jr.
Attorney, Agent, or Firm—Ann M. Kratz; Marvin Snyder

[57] ABSTRACT

An instrument for characterizing tumor tissue includes a broad-band light source, a monochromator for filtering collimated light from the broad-band light source, a scanner for scanning the monochromator through a range of predetermined wavelengths, and a hollow needle including a shaft with a tip on one end and a base on the other end. An optical fiber is positioned within the hollow needle for delivering light from the monochromator through the tip to a desired tissue region, A photodiode is mounted in the shaft and has a light sensitive surface facing outward from the shaft for detecting back-scattered light from the tissue region. The back-scattered light detected by the photodiode is monitored by a computer which records the optical absorption spectrum of light back-scattered from the tissue region at discrete locations in the tissue as the needle is inserted or withdrawn through the mammographically abnormal tissue.

19 Claims, 2 Drawing Sheets

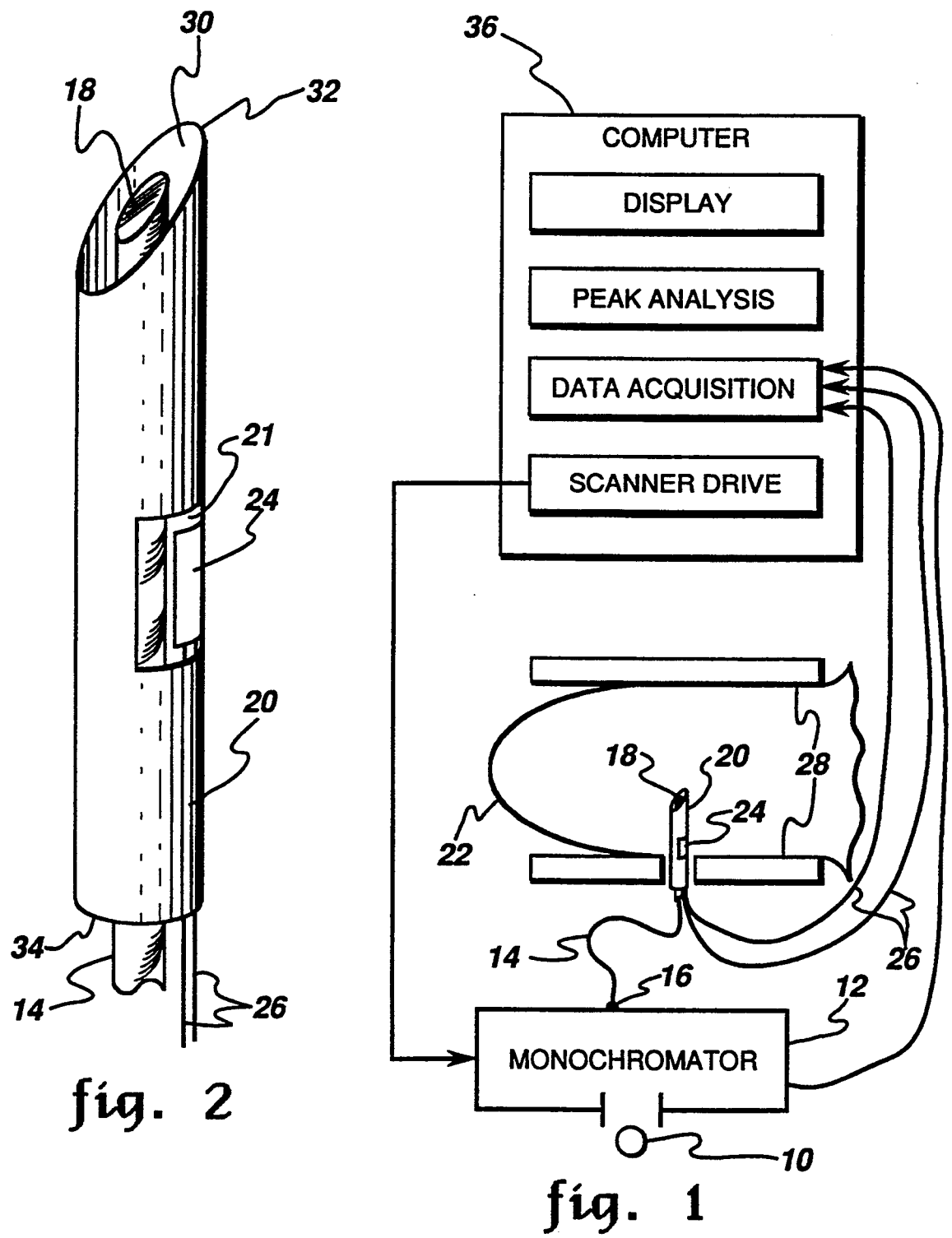

TUMOR TISSUE CHARACTERIZATION APPARATUS AND METHOD

BACKGROUND OF THE INVENTION

1. Field of the Invention

This invention relates generally to an instrument for diagnosing cancer, and, more particularly, to a hollow needle, including a fiber optic illuminator and a photodiode, for insertion into breast tissue to detect and analyze shifts in hemoglobin oxygenation.

2. Description of the Related Art

In a conventional procedure, a radiologist performs x-ray mammography. If an abnormal breast process recorded on the resulting mammograms is considered suspicious, a surgical biopsy can be ordered. Immediately prior to the biopsy, the radiologist takes several more views or projections of the breast during preoperative localization of the abnormality and marks the location of the suspicious abnormality by impaling the region with a thin, hooked guide wire. The patient is then taken to an operating room and a surgeon performing the biopsy follows the hooked wire guide to the precise location of the suspected abnormality. The most common form of biopsy involves surgically removing the suspected region. One of the less invasive forms of biopsy, stereotactic fine needle aspiration biopsy, aspirates a small amount of cells for cytologic analysis. The advantages of this technique are that it is minimally invasive, is accurate to less than 2 mm in lesion localization, has a sensitivity greater than 90%, and is less expensive than surgical biopsies. But since small (22 gauge) needles are used, cytology on the small amount of material removed is not easy. Far more accurate is large-core needle biopsy (using stereotactic positioning or ultrasound guidance), another alternative to surgical biopsy. Core biopsies remove a 1 mm×17 mm core of tissue (if a 14 gauge needle is used) for standard histological examination. However, benign histological diagnoses are difficult to make. In fact, for both fine needle aspiration biopsy and core biopsy, the techniques are only useful when they return a positive result for malignancy. In all other cases, the suspicious lesion must undergo incisional or excisional surgical biopsy.

False negatives in analyzing an x-ray mammogram occur when benign tumors or "normal" breast tissue with radiological densities similar to cancer completely or partially mask a malignant tumor which does not exhibit primary or secondary mammographic signs of carcinema. False positives are also problematic because they reduce the acceptability of mammography by the general public and lead to unnecessary biopsies.

Attempts have been made to use fibers to study biochemical and hemodynamic processes in tissues and to determine tissue type by using multiple fibers, one to deliver light and another to measure returning light. For example, see K. H. Frank et al., "The Erlangen micro-lightguide spectrophotometer EMPHO I," Phys. Med. Biol., vol. 34, No. 12, 1883–1900 (1989), Sung Chul Ji et al., "Micro-light guides: a new method for measuring tissue fluorescence and reflectance," American Journal of Physiology, vol. 236, C144–56 (March 1979); Kimizo One et al., "Fiber optic reflectance spectrophotometry system for in vive tissue diagnosis," Applied Optics, vol. 30, no. 1,98–105 (Jan. 1, 1991); and Irving J. Bigio et al., "The Optical Biopsy System," Los Alamos National Laboratory., Information Document (March 1992).

The optical absorption properties of malignant tissue differ in identifiable ways from those of normal and benign tissue, as described in F. A. Marks, "Optical determination of the hemoglobin oxygenation state of breast biopsies and human breast cancer xenographs in nude mice", SPIE Proceedings vol. 1641, 227–37 (January 1992). It would be useful to have an arrangement which measures optical absorption properties and has sufficient light detection capacity to perform a spectrum analysis in real time.

SUMMARY OF THE INVENTION

Accordingly, an object of the invention is to provide a minimally invasive means for obtaining an independent confirmation that mammographic abnormalities are benign or malignant with increased accuracy in regions where a radiographic mammogram has indicated the presence of suspicious breast processes.

Another object of the invention is to provide a needle-like instrument that can be inserted by a radiologist into a breast tissue region that is suspected of harboring an abnormal breast process and can yield diagnostically significant information about that tissue.

Briefly, according to a preferred embodiment of the invention, a tissue diagnostic instrument comprises a needle having a hollow shaft, a tip on one end of the shaft, a notch in the hollow shaft near the tip of the shaft, and a base on the other end of the shaft. An optical fiber is positioned within the hollow needle for delivering light of varying wavelengths in a predetermined range to a desired region of tissue through the tip. A photodetector with rod-like geometry is mounted in the notch of the shaft and has a light sensitive surface facing outward from the shaft for detecting back-scattered light from the desired region of tissue.

According to another preferred embodiment of the invention, an instrument for characterizing tumor tissue comprises a broad-band light source, a monochromator for filtering light from the broad-band light source, means for scanning the monochromator through a range of predetermined wavelengths, and a hollow needle including a shaft with a tip on one end of the shaft, a notch in the hollow shaft near the tip of the shaft, and a base on the other end of the shaft. A fiber is positioned within the hollow needle for delivering light from the monochromator through the tip to a desired region of the tissue. A photodiode with rod-like geometry is mounted in the notch of the shaft and has a light sensitive surface facing outward from the shaft for detecting back-scattered light from the illuminated region of the tissue. Means are provided for monitoring the back-scattered light detected by the photodiode and determining the spectral characteristics of the back-scattered light.

According to another preferred embodiment of the invention, a method for characterizing suspected mammographic-abnormalities comprises inserting into a region of the abnormal tissue a needle having a hollow shaft including a fiber positioned within the shaft and a photodiode mounted in the shaft having a light sensitive surface facing outward from the shaft. Light of varying wavelengths is supplied to the fiber. Back-scattered light from the region is detected by the photodiode. The detected back-scattered-light is monitored and the spectral characteristics of the back-scattered light are determined.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings, where like numerals represent like components, in which:

FIG. 1 is a schematic diagram of the diagnostic instrument of the invention;

FIG. 2 is a perspective view of one embodiment of the needle of the diagnostic instrument shown in FIG. 1;

DETAILED DESCRIPTION OF A PREFERRED EMBODIMENT OF INVENTION

Figure 3:
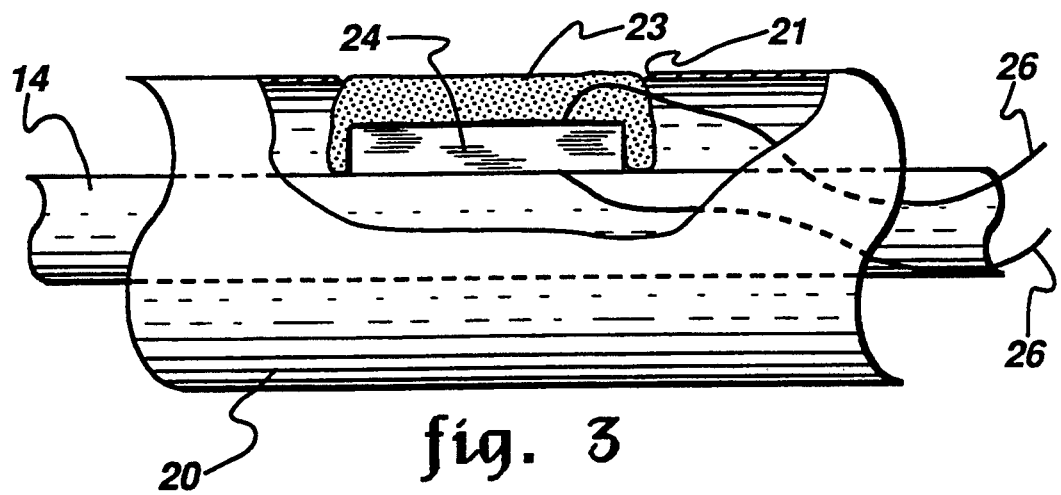
FIG. 3 is a sectional side view of one embodiment of the photodiode mount of the diagnostic instrument shown in FIG. 2.

In the apparatus shown in FIGS. 1 and 2, collimated light from an intense light source 10 is filtered by a monochromator 12 and focused on a fiber entrance 16 of an optical fiber 14 that is threaded down a shaft 30 of a hollow needle 20 having a photodiode 24. A computer 36 evaluates the light entering a test region and back-scattered light detected by photodiode 24 to characterize tissue in the test region.

Light source 10 is preferably a bright illuminator, such as a high pressure arc lamp or similar broad-band light source. Examples of appropriate light sources are a xenon arc lamp and a quartz tungsten-halogen lamp equipped with high efficiency light collection optics, as supplied by, for example, by Oriel Corp., Strafford, Conn. or Ealing Electrooptics Inc., Holliston, Mass.

Monochromator 12 filters collimated light from light source 10 and is scanned repetitively by a scanner drive (which may be part of computer 36, as shown) over the wavelength region that differentiates oxyhemoglobin from deoxyhemoglobin. Alternative methods of obtaining a spectrum of wavelengths include using a tunable dye laser and placing a plurality of filters, such as a motorized filter wheel, in front of a broad-band light source.

The wavelength region that includes the visible hemoglobin spectral bands is 340–700 nm. The Sorer absorption band of hemoglobin appears at 416 nm for oxyhemoglobin and at 431 nm for deoxyhemoglobin. The alpha and beta absorption bands appear at 577 and 542 nm respectively for oxyhemoglobin and as a single peak at 555 nm for deoxyhemoglobin. Other diagnostically significant spectral regions, such as, for example, the infrared hemoglobin spectral bands in the 700–1000 nm region (where a peak at 760 nm signifies deoxyhemoglobin), can be used, if desired. One choice of a sufficient sampling bandwidth range is 2 nm.

Needle 20 preferably comprises a modified soft tissue thin wall biopsy needle, and, for example, can be a stainless steel needle having a length of 5.5 inches (or any length greater than the depth of the lesion) from tip to base and diameter of 0.62 mm consistent with a 22 gauge Westcott biopsy needle. This type of needle is available from Becton-Dickinson, a division of Becton-Dickinson & Company, Rutherford, N.J. Needle 20 has a shaft 30 with a tip 32 at one end, a notch 21 in shaft 30, and a base 34 at the other end. Preferably tip 32 is cut at an angle consistent with commercially available biopsy needles for easy insertion into the tissue. Needle 20 is designed for insertion either by itself or through a 20 gauge ultra thin wall introducer needle (not shown) into a test region, shown as tissue of a breast 22 immobilized by compression plates 28. The needle typically has a hub (not shown) for ease of manipulation.

Optical fiber 14 is a multi-mode fiber having a fiber entrance 16 on which collimated light emerging from monochromator 12 is focused. Fiber 14 is threaded through base 34 of needle 20 and has a fiber exit 18, preferably polished, which is situated close to and preferably flush with needle tip 32. Fiber 14 preferably comprises a fused silica core (capable of transmitting light of wavelengths in the range of 340–1000 microns) with suitable cladding, such as silica, and is of a diameter of approximately 200 microns. Light travelling through fiber 14 emerges from fiber exit 18 and illuminates suspected tissue, resulting in subsequent absorption and scattering of the light by the tissue.

A photodetector, shown as photodiode 24, is mounted on needle shaft 30 and has an optically sensitive surface facing outward from shaft 30 so as to be exposed to back-scattered light from tissue 22. Photodiode 24 is mounted in notch 21 which is near needle tip 32, preferably a few millimeters, such as 2–8 mm, for example, from needle tip 32.

One method of mounting a photodiode is illustrated in the embodiment of FIG. 3. Photodiode 24 is inserted into a notch 21 in a side of needle 20 already having a fiber 14. Photodiode leads 26 are wire bonded to the photodiode and are fed down the shaft of the needle. The hole is filled and the photodiode is covered with clear epoxy 23 which is then set and polished until the epoxy is flush with the needle.

In a preferred embodiment, photodiode 24 is long and thin so that its geometry conforms to that of needle 20, and thus an increased active area of the photodiode is achieved without changing the diameter of needle shaft that is required to hold the photodiode. The photodiode can be 200 microns wide and have a length such that the path length differences of detected photons of the same wavelength is less than the spatial resolution required for adequate diagnosis. Use of a photodiode, as opposed to an optical fiber, provides a larger light collection area and an increase in the acceptance angle of the detector, thus improving sensitivity and signal-to-noise ratio for the instrument. If desired, a plurality of photodiodes can be used for collecting a greater portion of the back-scattered light.

Computer 36 receives data from photodiode 24 through photodiode leads 26. If monochromator 12 does not have its own scanner drive, computer 36 functions as a scanner drive. Regardless of whether the computer drives the scanner, the computer is coupled to the monochromator so that the computer receives data relating to which wavelength of light is being used at a particular instant in time. Computer 36 uses data relating to light entering the system through fiber 14 and back-scattered light being detected by photodiode 24 to record wavelength and amplitudes of significant peaks of the absorption spectrum of the back-scattered light.

In this way, tissue 22 can be continually monitored as needle 20 is being inserted or withdrawn, and real time processing is achieved. If a profound shift in tissue oxygenation occurs from normal saturation levels to nearly unsaturated hemoglobin, then the tumor tissue can be diagnosed as having a high probability of malignancy, If there is no shift, the lesion can be diagnosed as benign. This evaluation is based on the fact that absorption properties for malignant tissue differ in that a higher fraction of de-oxygenated blood can be found in the tissue of a malignant tumor. This deoxygenation can be caused by high metabolic rates and by the relatively disorganized state of blood vessels, both structurally and in terms of heterogeneous microcirculation, in and around a tumor.

Certain spectral bands are of particular significance when evaluating blood oxygenation. For example, the Soret band is red-shifted as blood becomes deoxygenated. An absorption peak is red-shifted when the position of its maximum or centroid moves towards the long wavelength end of the visible spectrum in response to a stimulus, and an absorption peak is blue-shifted when the peak shifts in position on the wavelength scale towards the short wavelength end of the visible spectrum. Thus, rather than being at a wavelength of 416 nm, the wavelength of the Soret band peak moves closer to 431 nm as the needle moves into a tumor containing a high fraction of deoxygenated hemoglobin. Additionally, the alpha and beta peaks (at wavelengths of 577 and 542 nm respectively) of oxyhemoglobin merge into a single band at a wavelength of 555 nm as oxygen is reduced. The existence of an absorption peak at 760 nm also denotes presence of deoxyhemoglobin.

A radiologist can thus identify the tissue type (malignant or benign) of the tumor by inserting the needle into the tissue and comparing the spectrum when the needle is outside the suspected region with the spectrum when the needle is inside the suspected region.

In one embodiment, an initial mammogram is obtained using a fenestrated compression plate, and the position of the lesion or abnormal region is marked in x and y coordinates. An introducer needle of appropriate length is inserted through a window in the compression plate over the marked spot deep into the tissue so that its tip passes beyond the suspected region. The breast is uncompressed slowly and recompressed in an orthogonal projection. Other mammograms are taken to ensure that the introducer needle is positioned so that its tip is approximately 1 cm beyond the lesion. The tissue diagnostic instrument is inserted through the introducer needle to the same depth within the breast as the introducer needle. The introducer needle is removed and, with the breast still under compression, the tissue diagnostic instrument is withdrawn in steps of several min. At each step, an optical absorption spectrum is recorded.

Figure 4:
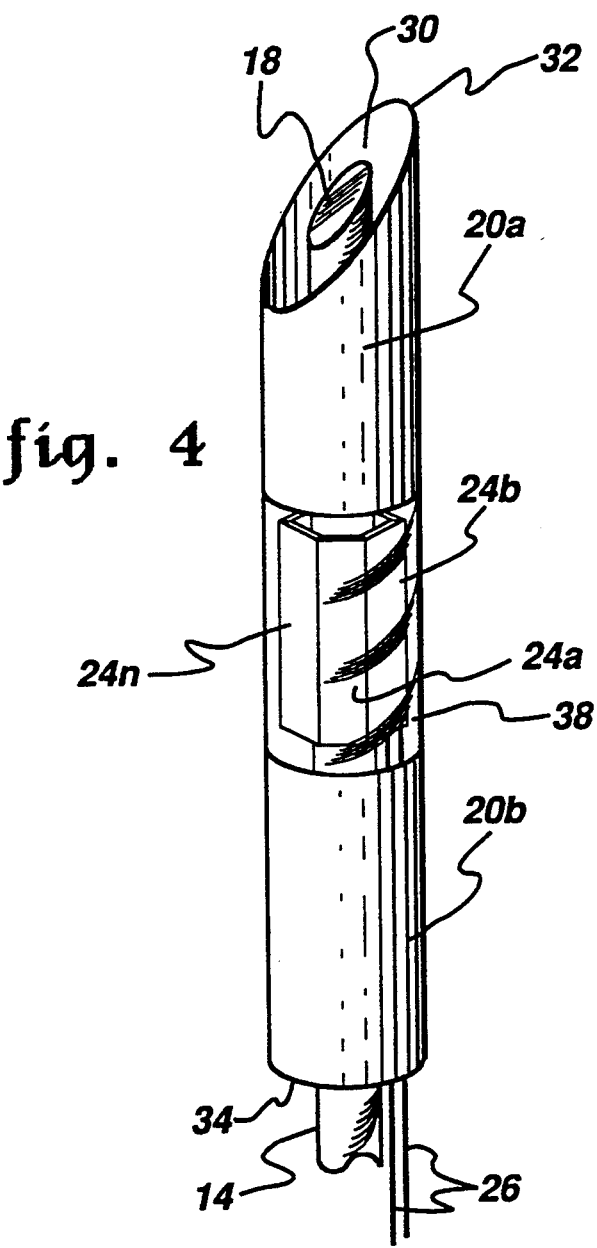
FIG. 4 is a perspective view of another embodiment of the needle of the diagnostic instrument shown in FIG. 1.

FIG. 4 is a perspective view of another embodiment of the needle of the diagnostic instrument shown in FIG. 1, designed to increase the signal-to-noise ratio of the instrument. This embodiment is similar to the embodiment of FIG. 2, except for the method of mounting the photodiode or photodiodes in needle shaft 30. In this embodiment, shaft 30 includes three portions. Tip portion 20a and base portion 20b are situated on opposite ends of a hollow cylinder 38 which has a diameter substantially equal to the diameter of the tip and base portions and comprises an optically transparent material. The three portions are brazed together before fiber 14 is inserted. Within hollow cylinder 38, a plurality n of long, thin, planar photodiodes 24a, 24b . . . 24n are arranged in a polygon around the perimeter and electronically linked so as to provide the sum intensity of all back-scattered light incident on the cylinder from up to $4\pi$ steradians.

Needle shaft 30 must be structurally strong enough to allow for insertion into breast tissue. Thus, either the photodiodes will have strong substrates, such as metal, or the hollow cylinder will comprise a very strong material, such as sapphire.

While only certain preferred features of the invention have been illustrated and described herein, many modifications and changes will occur to those skilled in the art. For example, other methods instead of using a notch or hollow cylinder may be used to mount a photodiode. It is, therefore, to be understood that the appended claims are intended to cover all such modifications and changes as fall within the true spirit of the invention.

What is claimed is:

1. A tissue diagnostic instrument, comprising:
   a needle having a hollow shaft, a tip on one end of said shaft, and a base on the other end of said shaft;
   an optical fiber positioned within said shaft for delivering light of varying wavelengths in a predetermined range to a desired region of tissue through said tip; and
   a photodetector mounted in said shaft and having a light sensitive surface facing outward from a side of said shaft for detecting back-scattered light from said desired region of tissue.

2. The instrument of claim 1, wherein said photodetector comprises a photodiode.

3. The instrument of claim 2, further including a monochromator for supplying said light of varying wavelengths to said fiber.

4. The instrument of claim 3, further including means for scanning said monochromator through said predetermined range of wavelengths.

5. The instrument of claim 4, further including a broad-band light source for supplying light to said monochromator.

6. The instrument of claim 5, wherein said light source is selected from the group consisting of a quartz tungsten-halogen lamp and a xenon arc lamp.

7. The instrument of claim 2, wherein said needle tip is angled.

8. The instrument of claim 2, wherein said fiber has a polished exit surface.

9. The instrument of claim 8, wherein said exit surface is situated substantially flush with respect to said tip of said needle.

10. The instrument of claim 2, including means for monitoring the back-scattered light detected by said photodiode and determining the optical absorption properties in said region of tissue.

11. The instrument of claim 10, wherein said shaft comprises a tip portion including said tip, a base portion, including said base, and an optically transparent hollow cylinder situated between said tip and base portions, said hollow cylinder containing said photodiode and at least one additional photodiode coupled to said monitoring means.

12. The instrument of claim 11, wherein said hollow cylinder has a diameter substantially equal to the diameters of said tip portion and said base portion.

13. The instrument of claim 12, wherein said hollow cylinder comprises sapphire.

14. An instrument for characterizing a tumor in breast tissue, comprising:

a broad-band light source capable of delivering varying wavelengths in a predetermined range;

a needle having a hollow shaft, a tip on one end of said shaft, and a base on the other end of said shaft;

an optical fiber positioned within said hollow needle for delivering light from said light source through said tip to a desired region of tissue;

a photodiode mounted in said shaft and having a light sensitive surface facing outward from a side of said shaft for detecting back-scattered light from said region of tissue; and means for monitoring the back-scattered light detected by said photodiode and determining the spectral characteristics of the back-scattered light in said region of tissue.

15. The instrument of claim 14, wherein said broad-band light source includes:

a lamp selected from the group consisting of a quartz tungsten-halogen lamp and a xenon arc lamp;

a monochromator for filtering light from said lamp; and a scanner drive for scanning said monochromator through a predetermined range of wavelengths.

16. The instrument of claim 15, wherein said shaft comprises a tip portion including said tip, a base portion, including said base, and a hollow cylinder situated between said tip and base portions, said hollow cylinder containing said photodiode and at least one additional photodiode coupled to said monitoring means, said hollow cylinder having a diameter substantially equal to the diameters of said tip portion and said base portion.

17. A method for characterizing mammographically abnormal tissue, comprising the steps of:

inserting into a region of suspected abnormal tissue a hollow needle comprising a shaft including an optical fiber positioned within said shaft and a photodetector mounted in said shaft having a light sensitive surface facing outward from a side of said shaft;

supplying light of varying wavelengths to said fiber;

detecting back-scattered light from said tissue region with said photodetector; and monitoring the back-scattered light detected by said photodetector and determining the spectral characteristics of the back-scattered light in said region of tissue.

18. The method of claim 17, wherein said tumor tissue comprises breast tissue, and further including the step of, prior to inserting said needle into said region of suspected tumor tissue, compressing said breast tissue.

19. The method of claim 18, wherein said varying wavelengths have a range from selected from the group consisting of 340 nm–700 nm and 700 nm–1000 nm.

* * * * *